(12) United States Patent
Kapin et al.

(10) Patent No.: US 6,271,224 B1
(45) Date of Patent: Aug. 7, 2001

(54) USE OF CERTAIN ISOQUINOLINESULFONYL COMPOUNDS FOR THE TREATMENT OF GLAUCOMA AND OCULAR ISCHEMIA

(75) Inventors: Michael A. Kapin, Arlington; Louis M. Desantis, Jr., Fort Worth, both of TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/077,575

(22) PCT Filed: Dec. 20, 1996

(86) PCT No.: PCT/US96/20197

§ 371 Date: Jan. 19, 1999

§ 102(e) Date: Jan. 19, 1999

(87) PCT Pub. No.: WO97/23222

PCT Pub. Date: Jul. 3, 1997

Related U.S. Application Data

(60) Provisional application No. 60/009,351, filed on Dec. 21, 1995.

(51) Int. Cl.$^7$ .................................................. A61K 31/55
(52) U.S. Cl. ........................... 514/218; 514/912; 514/913
(58) Field of Search .................................. 514/218, 912, 514/913

(56) References Cited

U.S. PATENT DOCUMENTS

| | | |
|---|---|---|
| 4,525,589 | 6/1985 | Hidaka et al. . |
| 4,540,408 | 9/1985 | Lloyd . |
| 4,678,783 | 7/1987 | Hidaka et al. . |
| 4,730,013 | 3/1988 | Bondi et al. . |
| 4,911,920 | 3/1990 | Jani et al. . |
| 5,212,162 | 5/1993 | Missel et al. . |
| 5,552,403 | 9/1996 | Burke et al. . |
| 5,573,758 | 11/1996 | Adorante et al. . |
| B1 4,678,783 | 4/1995 | Hidaka et al. . |

FOREIGN PATENT DOCUMENTS

| | | |
|---|---|---|
| 7277979 | 10/1995 | (JP) . |
| WO 93/23082 | 11/1993 | (WO) . |
| WO 94/13275 | 6/1994 | (WO) . |
| WO 95/15958 | 6/1995 | (WO) . |
| WO 95/19968 | 7/1995 | (WO) . |
| WO 96/17608 | 6/1996 | (WO) . |

OTHER PUBLICATIONS

Derwent Abstract, JP 7238071 (Sep. 12, 1995), DIALOG® File No. 351, Accession No. 10447021.

*Drugs of the Future*, "Fasudil Hydrochloride" 17(12):1132–1133 XP 000617424 (1992).

*Primary Examiner*—Zohreh Fay
(74) *Attorney, Agent, or Firm*—Barry L. Copeland

(57) ABSTRACT

The present invention relates to the field of ophthalmology. In particular the invention relates to the field of ocular disorders including visual field loss and glaucoma using an isoquinolinesulfonyl compound, which lowers intraocular pressure (IOP) and produces dilation of ocular blood vessels.

9 Claims, No Drawings

USE OF CERTAIN ISOQUINOLINESULFONYL COMPOUNDS FOR THE TREATMENT OF GLAUCOMA AND OCULAR ISCHEMIA

This application is a 371 of PCT/US96/20197 filed on Dec. 20, 1996. This application claim benefit to Provisional Application No. 60/009,351 filed Dec. 21, 1995,

BACKGROUND OF THE INVENTION

Although the underlying causes of glaucoma are not fully understood at this time, glaucoma is characterized by damage to the optic nerve head, accompanied by a decrease in the normal visual field. One risk factor for glaucomatous visual field loss is elevated IOP. In fact, glaucoma has historically been treated by drug and/or surgical therapy to lower elevated IOP. While elevated IOP has been positively correlated with the rate of progression of visual field loss in glaucoma, visual field loss may occur at levels of IOP which are considered within the normal range. Thus, other factors, alone or in addition to elevated IOP, may influence the occurrence and rate of progression of visual field loss.

To remain healthy and function normally, the retina and the optic nerve head fibers (neurons) must receive a proper supply of nutrients and oxygen, and must have their carbon dioxide and other metabolic waste products removed. This is accomplished by the microcirculation in these tissues. As used herein, the term "microcirculation" refers to the blood flow through the nutritive blood vessels, across whose walls nutrients, gases and waste products move. Blood flow to the eye depends upon the pension pressure (the systemic blood pressure may the IOP). Some tissues have the ability to maintain (i.e., autoregulate) blood flow through a range of perfusion pressures such that an increase in systemic blood pressure may cause a reduction in the caliber of the blood vessel lumen. Conversely, reduction in systemic pressure in such tissues can result in vessel dilation; however, there is a point where perfusion pressure falls to such a level that the vessel is maximally dilated. Any further fall in perfusion pressure results in a reduction of blood flow to the tissue (ischemia). Ischemia may also result from obstruction, vasospasm, increased vascular resistance, or other interference with microcirculation. Prolonged ischemia ultimately can result in tissue necrosis or neuronal cellular apoptosis. In the case of the optic nerve head or retina, a state of visual dysfunction may precede the death of the neurons. Hence, if ischemia is involved in the death of optic nerve fibers due to glaucoma or some other ischemic-borne retinopathies or optic neuropathies, then its prevention could protect the neurons from death or loss of function.

The vasodilatory and spasmolytic activities of certain isoquinolinesulfonyl compounds have been described with respect to non-ocular tissues. See, e.g., EP 0 187 371 B1, which corresponds to U.S. Pat. No. 4,678,783. These vascular attributes are likely associated with inhibitition of myosin-light chain kinase activity. Myosin-light chain kinase is an enzyme necessary for the excitation-contraction coupling of contractile activity in vascular smooth muscle. Inhibition of this enzyme results in vascular smooth muscle relaxation (i.e., vasodilation) which can produce an increased blood flow.

SUMMARY OF THE INVENTION

The inventors believe that microcirculatory disturbances that restrict nutritive blood flow to the choroid, retina and optic nerve head are likely involved in the progression of visual field loss. While bound by no theories, the inventors postulate that compounds which enhance oxygen and nutrient delivery by enhancing ocular blood flow may be beneficial in preventing optic nerve head injury and may subsequently prevent or alter the rate of progression of visual field loss associated with glaucoma and ischemic optic neuropathies.

The present invention provides compositions and methods useful in the treatment of glaucoma (with or without ocular hypertension) and ocular ischemia, which may result in retinopathies and optic neuropathies. The compositions contain an isoquinolinesulfonyl compound which is effective in reducing or preventing optic nerve head or retinal damage as well as reducing IOP toward normal levels and thus, in reducing or preventing visual field loss.

In an alternative embodiment of the compositions and methods of the present invention, the above compositions may further include a mucomimetic polymer, a gelling polysaccharide, a finely divided drug carrier substrate (defined below), or a combination of these components. These additional components provide compositions which enhance comfort and provide sustained release and delivery of the drug to the eye.

DETAILED DESCRIPTION OF THE INVENTION

Elevation of IOP is associated with clinical manifestations characteristic of glaucomatous optic neuropathy. Optic nerve dysfunction may be the result of pressure-induced changes in the structure of the optic nerve head and/or reduced circulation to the optic nerve head and retina. In addition to affecting vascular resistance and blood flow, the inventors have discovered that certain isoquinolinesulfonyl compounds also lower intraocular pressure.

The isoquinolinesulfonyl compounds of the present invention are the compounds of formula (I) shown below, as well as their pharmaceutically acceptable salts.

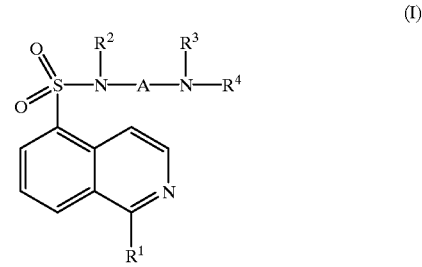

(I)

wherein
  $R^1$ represents a hydrogen atom, a chlorine atom or a hydroxyl group; and when $R^1$ represents a hydrogen atom,
  A represents an ethylene group unsubstituted or substituted with an alkyl group having 1 to 6 carbon atoms, a phenyl group or a benzyl group,
  $R^2$ and $R^3$ are directly bonded with each other, thereby forming a trimethylene group unsubstituted or substituted with an alkyl group having 1 to 6 carbon atoms, a phenyl group or a benzyl group, and
  $R^4$ represents a hydrogen atom or an alkyl group having 1 to 6 carbon atoms; and
when
  $R^1$ represents a chlorine atom or a hydroxyl group,
  A represents an alkylene group having 2 to 6 carbon atoms, said group being unsubstituted or substituted with an alkyl group having 1 to 6 carbon atoms, $R^2$ and $R^3$ are not bonded with each other and each independently represent a hydrogen atom or an alkyl group having 1 to 6 carbon atoms, or $R^2$ and $R^3$ are directly bonded with each other, thereby forming an ethylene group unsubstituted or substituted with an alkyl group having 1 to 6 carbon atoms or a trimethylene group unsubstituted or substituted with alkyl group having 1 to 6 carbon atoms, and $R^4$ represents a hydrogen atom, an alkyl group having 1 to 6 carbon atoms or an amidino group;

and pharmaceutically acceptable salts thereof. With respect to the above-mentioned alkyl groups, they may be a straight chain group or a branched chain group. These compounds and methods of their syntheses are disclosed in U.S. Pat. No 4,678,783, the entire contents of which are incorporated herein by this reference. Other isoquinolinesulfonyl derivatives and methods of their syntheses are disclosed in U.S. Pat. No. 4,525,589, the entire contents of which are likewise incorporated herein by this reference.

The preferred isoquinohnesulfonyl compound of the present invention is hexahydro-1-(5-isoquinolinylsulfonyl)-1H-1,4-diazepine, also known as 1-(5-isoquinolinesulfonyl)-homopiperazine, and shown below as Compound (II), as well as its pharmaceutically acceptable salts.

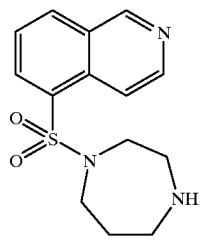

(II)

Most preferred is the hydrochloride salt of Compound (II). The hydrochloride salt of Compound (II), known as fasudil, AT-877, and HA-1077 is manufactured by Asahi Chemical Industry Co., Ltd. (Japan).

Alternatively, Compound (II) and a preferred metabolite thereof may be represented the following formula:

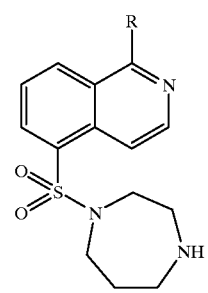

(III)

wherein R=H or OH.

In general, for topical administration an amount of an isoquinolinesulfonyl compound between about 0.001 and about 10.0 percent by weight (wt %) is used in the compositions of the present invention. It is preferred that between about 0.01 and about 3.0 wt % is used, and it is especially preferred to use an amount between about 0.1 and about 2.0 wt %.

The compositions of the present invention may additionally include components to provide sustained release and/or comfort. Such components include mucomimetic polymers, gelling polysaccharides and finely-divided drug carrier substrates. These components are discussed in greater detail in U.S. Pat. No. 4,911,920 issued Mar. 27, 1990 and in U.S. Pat. No. 5,212,162 issued May 18, 1993. The entire contents of these two patents are incorporated herein by reference. For purposes of this invention, the term "mucomimetic polymers" includes carbomers (discussed below), mucopolysaccharides (e.g. hyaluronic acid and chondroitin sulfate) and cellulosic polymers (e.g. methyl cellulose, hydroxy propyl methyl cellulose, hydroxyethyl cellulose, carboxy methyl cellulose, and hydroxy propyl cellulose).

The preferred mucomimetic polymers useful in the present invention are anionic and have a molecular weight between about 50,000 and 6 million daltons. These preferred polymers are characterized as having carboxylic acid functional groups and preferably contain between 2 and 7 carbon atoms per functional group. The gels which form during preparation of the ophthalmic polymer dispersion have a viscosity between about 1,000 to about 300,000 centipoise (cps). Suitable polymers are carboxy vinyl polymers, preferably those called carbomers, e.g., CARBOPOL® (Goodrich Co., Cleveland, Ohio). Specifically preferred are CARBOPOLO® 934 and 940. Such polymers will typically be employed in an amount between about 0.05 and about 8.0 wt %, depending on the desired viscosity of the composition. Pourable liquid compositions generally comprise an amount of the polymer between about 0.05 and about 2.0 wt %.

As used herein, the term "finely-divided drug carrier substrate" (or "DCS") means finely-divided solids, colloidal particles, or soluble polymers and/or polyelectrolytes which are capable of selective adsorption or binding with drug molecules. Examples of DCS include, but are not limited to: finely divided silica, such as fumed silica, silicates and bentonites; ion exchange resins, which can be anionic, cationic or non-ionic in nature; and soluble polymers, such as, alginc acid, pectin, soluble carrageenans, CARBOPOL®, and polystyrene sulfonic acid. In general, the DCS component is used at a level in the range of about 0.05 to about 10.0 wt %. For particulate DCS, the average particle size diameter ranges from about 1 to about 20 microns. The amount of DCS and its characteristics (e.g., amount of cross-linking, particle size) may be varied in order to produce the desired time-release profile for the chosen drug.

Preferred DCS are the ion exchange resins. Some resins which are used in chromatography make ideal DCS for binding drugs in the compositions of the present invention. Such resins are readily available, for example, from Rohm & Haas (Philadelphia, Pa.) under the name AMBERLITE® and from Dow Chemical Co. (Midland, Mich.) under the name DOWEX®. The average particle size diameter of the commercially available forms of the resins is about 40 to about 150 microns. Such commercially available particles are most conveniently reduced to a particle size range of about 1.0 to about 25 microns by ball milling, according to known techniques. At least 95% of the resulting spheroidal particles will preferably have a diameter less than 20 microns. The ion exchange resins will typically be present in an amount between about 0.05 and about 10.0 wt % and will have an average particle size diameter between about 1 and about 20 microns.

In addition to the above-described principal ingredients, the compositions of the present invention may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, polyquaternium 1 and other agents equally well-known to those skilled in the art. Such preservatives, if utilized, will typically be employed in an amount between about 0.001 and about 1.0 wt %. Examples of suitable agents which may be utilized to adjust the tonicity or osmolality of the formulations include: sodium chloride, potassium chloride, mannitol, dextrose, glycerin and propylene glycol. Such agents, if utilized, will typically be employed in an amount between about 0.1 and about 10.0 wt %.

As will be appreciated by those skilled in the art, the compositions may be formulated in various dosage forms suitable for topical ophthalmic delivery, including solutions, suspensions, emulsions, gels and erodible solid ocular inserts. The compositions are preferably aqueous, have a pH between about 3.5 and about 8.0 and an osmolality between about 280 and about 320 milliOsmoles per kilogram (mOsm/kg).

The compositions of the present invention may also comprise non-aqueous formulations such as: substantially non-aqueous liquids, substantially non-aqueous semi-solid compositions, and solid compositions or devices. The first class, substantially non-aqueous liquids, includes a isoquinolinesulfonyl compound dissolved or suspended in one or more of the following: vegetable and mineral oils, such as liquid petrolatum, corn oil, castor oil, sesame oil, and peanut oil; triglycerides, such as the capric/caprylic triglycerides commonly used in foods and cosmetics; liquid lanolin and lanolin derivatives; and perfluorohydrocarbons. The second class, semi-solid compositions, comprises an isoquinolinesulfonyl compound dissolved or suspended in one or more of the following: various types of petrolatum, such as white, yellow, red, and so on; lanolin and lanolin derivatives; gelled mineral oil having a hydrocarbon base, such as PLASTIBASES®; petrolatum and ethylene carbonate mixtures; petrolatum in combination with surfactants and polyglycol, such as polyoxyl 40 stearate and polyethylene glycol.

The third class, solid compositions or devices, includes an isoquinolinesulfonyl compound in association with (i) non-erodible devices which are inserted into the conjunctival sac of the eye and later removed, such as the Alza-type diffusion or osmotic pressure controlled polymer membranes; and (ii) bioerodible polymers which do not have to be removed from the conjunctival sac, such as essentially anhydrous but water soluble polymers and resins (e.g., celluloses, polycarboxylic acids, and so on). Especially preferred are the bioerodible inserts described and detailed in U.S. Pat. No. 4,540,408 (Lloyd) and U.S. Pat. No. 4,730,013 (Bondi et al.), wherein isoquinolinesulfonyl compounds of the present invention would be entrained in a non-aqueous matrix consisting essentially of polyvinyl alcohol. The entire contents of these two patents are incorporated herein by reference.

As will further be appreciated by those skilled in the art, the isoquinolinesulfonyl compounds of the present invention may also be administered intraocularly, periocularly or systemically (e.g. parenterally or orally).

Intraocular or periocular administration may be effected by incorporating a isoquinolinesulfonyl compound in a surgical irrigating solution used in ophthalmic surgery, or, preferably, by intravitreal or periocular injection. Such injection therapy will typically require from about 0.1 nM to about 1 mM (approximately 0.02 ng to 500 $\mu$g) of a isoquinolinesulfonyl compound for each eye treated. It is preferred that between about 200 nM and about 160 $\mu$M (approximately 40 ng to 80 $\mu$g) per eye be used in such therapy.

The preferred routes of systemic administration are oral and intravenous. Oral dosing of an isoquinolinesulfonyl compound in accordance with this invention will typically range from about 1.0 to about 1000 mg, one to four times per day. The preferred dosing range of oral administration is from about 10 to about 250 mg two to three times per day. Intravenous dosing of an isoquinolinesulfonyl compound in accordance with this invention will typically range from about 0.01 to about 100 mg, one to four times per day. The preferred dosing range for intravenous administration is from about 1.0 to about 30 mg, two to three times per day.

The present invention is also directed to methods of treating glaucoma and other ophthalmic diseases and abnormalities associated with vial field loss. The treatment may be effected by administering a therapeutically effective amount of an isoquinolinesulfonyl compound topically, intraocularly, periocularly or systemically. The preferred methods comprise topically applying to the affected eye(s) of the patient a therapeutically effective amount of a composition according to the present invention. The frequency and amount of dosage will be determined by the clinician based on various clinical factors. The preferred methods will typically comprise topical application of one or two drops (or an equivalent amount of a solid or semi-solid dosage form) to the affected eye as needed, preferably one to three times per day.

The following examples are presented to further illustrate various aspects of the present invention, but are not intended to limit the scope of the invention in any respect.

EXAMPLE 1

The hydrochloride salt of Compound II, also known as fasudil hydrochloride or just fasudil, was topically administered to eyes of ocular hypertensive monkeys, New Zealand Albino (NZA) and Dutch Belted (CB) rabbits. The results are presented in Table 1. As presented, Compound II effectively lowered IOP in both ocular normotensive and hypotensive (laser-induced) primates. In NZA rabbits, IOP was marketedly lowered below base line for the four hour dose response. Compound II also lowered IOP in the DB rabbit; however, the reduction in IOP was not sustained as in the NZA rabbit study.

TABLE 1

EFFECT OF FASUDIL ON IOP REDUCTION IN THE OCULAR HYPERTENSIVE AND NORMOTENSIVE MONKEY, NEW ZEALAND ALBINO AND DUTCH BELTED RABBIT

| ANIMAL MODEL | Baseline IOP (mmHg) | PERCENT CHANGE FROM BASELINE | | | | |
| --- | --- | --- | --- | --- | --- | --- |
| | | 1 HR | 2 HR | 3 HR | 4 HR | 6 HR |
| Lasered MIOP (n = 9)† | 32.1 ± 3.2 | 21.9 ± 6.7↓ | — | 14.6 ± 6.5↓ | — | 23.4 ± 4.4↓ |
| Lasered MIOP (n = 9) | 38.2 ± 3.3 | 15.9 ± 6.8↓ | — | 16.1 ± 4.8↓ | — | 7.1 ± 4.9↓ |

TABLE 1-continued

EFFECT OF FASUDIL ON IOP REDUCTION IN THE OCULAR HYPERTENSIVE AND NORMOTENSIVE MONKEY, NEW ZEALAND ALBINO AND DUTCH BELTED RABBIT

| ANIMAL MODEL | Baseline IOP (mmHg) | PERCENT CHANGE FROM BASELINE | | | | |
|---|---|---|---|---|---|---|
| | | 1 HR | 2 HR | 3 HR | 4 HR | 6 HR |
| Normal MIOP (n = 9) | 20.4 ± 1.4 | 18.9 ± 5.5↓ | — | 21.7 ± 5.2↓ | — | 11.1 ± 5.3↓ |
| Dutch Belted Rabbit (n = 7)†† | 37.4 ± 0.6 | 33.7 ± 2.1↓ | 18.0 ± 3.7↓ | 10.8 ± 5.2↓ | 6.6 ± 3.9↓ | — |
| Dutch Belted Rabbit (n = 7)†† | 32.1 ± 0.4 | 33.1 ± 2.7↓ | 25.2 ± 3.5↓ | 16.7 ± 3.9↓ | 11.7 ± 4.0↓ | — |
| NZA Rabbit (n = 7)†† | 27.2 ± 0.3 | 36.2 ± 3.7↓ | 35.5±3.6↓ | 26.1 ± 3.9↓ | 22.5 ± 3.8↓ | — |

All drugs were administered to eyes in a topical manner at a dose = 500 μg (2 × 25 μl). Fasudil was formulated in phosphate buffered saline containing 0.01% benzalkonium chloride. † No significant change in IOP from baseline values was observed in the contralateral untreated ocular normotensive eye or in a vehicle treated ocular hypertensive eye. †† No significant change in IOP from baseline values were observed in the contralateral untreated eye. MIOP = monkey intraocular pressure. n = number of animals in study.

EXAMPLE 2

Compound II (hydrochloride) was administered topically to the eyes of Dutch Belted (DB) rabbits in doses of 75 and 150 μg. The results are presented in Table 2.

TABLE 2

DOSE-RESPONSE STUDIES OF FASUDIL ON IOP IN THE DUTCH BELTED RABBIT

| Compound | Baseline IOP (mmHg) | Percent Change from Baseline | | | | |
|---|---|---|---|---|---|---|
| | | 0.5 hr | 1 hr | 2 hr | 3 hr | 4 hr |
| Group 1 Fasudil 150 μg OD | 33.0 ± 0.8 | 8.8 ± 3.8↓ | 11.5 ± 3.2↓ | 14.6 ± 3.5↓ | 3.4 ± 2.7↓ | 0.5 ± 3.2↑ |
| Group 1 Vehicle OS | 33.8 ± 0.6 | 3.6 ± 1.9↓ | 3.7 ± 2.4↓ | 5.7 ± 2.6↓ | 0 ± 2.4↓ | 2.1 ± 3.2↑ |
| Group 2 Fasudil 75 μg OD | 34.3 ± 0.8 | 3.2 ± 2.8↓ | 3.3 ± 1.9↓ | 1.7 ± 2.7↓ | 5.2 ± 2.2↓ | 2.9 ± 2.1↓ |
| Group 2 Vehicle OS | 33.8 ± 0.6 | 1.1 ± 0.6↑ | 5.9 ± 2.6↑ | 6.0 ± 3.9↑ | 4.5 ± 1.9↑ | 1.9 ± 3.4↑ |

All drugs were administered to eyes in a topical manner (1 × 30 μl). All compounds were formulated in a phosphate buttered saline containing 0.01% benzalkonium chloride. N = 6 animals/group; OD = drug treated eye; OS = vehicle treated contralateral eye.

EXAMPLE 3

A dose study similar to that described in Example 2 was conducted with the NZA rabbit. Compound II (hydrochloride) was administered in a topical ocular fashion in doses of 50, 125 and 250 μg. The results of this study are presented in Table 3.

TABLE 3

DOSE-RESPONSE STUDIES OF FASUDIL ON IOP IN THE NEW ZEALAND ALBINO RABBIT

| Compound | Baseline IOP (mmHg) | Percent Change from Baseline | | | | |
|---|---|---|---|---|---|---|
| | | 0.5 hr | 1 hr | 2 hr | 3 hr | 4 hr |
| Group 1 Fasudil 250 μg OD | 20.6 ± 0.3 | 5.5 ± 6.7↓ | 21.1 ± 5.4↓ | 24.9 ± 6.1↓ | 25.1 ± 4.1↓ | 16.3 ± 4.0↓ |

TABLE 3-continued

DOSE-RESPONSE STUDIES OF FASUDIL ON IOP
IN THE NEW ZEALAND ALBINO RABBIT

| Compound | Baseline IOP (mmHg) | Percent Change from Baseline | | | | |
|---|---|---|---|---|---|---|
| | | 0.5 hr | 1 hr | 2 hr | 3 hr | 4 hr |
| Group 2 Vehicle OS | 21.2 ± .5 | 1.1 ± 3.7↓ | 4.4 ± 3.4↑ | 2.7 ± 3.2↑ | 2.7 ± 3.9↑ | 5.4 ± 3.6↑ |
| Group 2 Fasudil 125 μg OD | 20.4 ± .7 | 2.8 ± 3.8↑ | 11.6 ± 2.9↓ | 11.0 ± 4.7↓ | 7.0 ± 4.8↓ | 5.1 ± 2.7↓ |
| Group 2 Vehicle OS | 21.3 ± .6 | 5.3 ± 2.6↑ | 8.3 ± 6.0↑ | 7.3 ± 4.6↑ | 7.2 ± 5.3↑ | 17.1 ± 6.5↑ |
| Group 3 Fasudil 50 μg | 21.3 ± .5 | 1.6 ± 3.0↓ | 3.2 ± 3.1↑ | 2.1 ± 4.7↑ | 1.7 ± 4.3↓ | 10.8 ± 5.7↑ |
| Group 3 Vehicle OS | 21.4 ± .8 | 6.7 ± 4.1↑ | 9.1 ± 1.7↑ | 3.6 ± 3.3↑ | 9.8 ± 7.6↑ | 7.4 ± 4.5↑ |

All drugs were administered to eyes in a topical manner (1 × 30 μl). All compounds were formulated in a phosphate buttered saline containing 0.01% benzalkonium chloride. N = 6 animals/group; OD = drug treated eye; OS = vehicle treated contralateral eye.

EXAMPLE 4

The effect of repeated doses of Compound II on the magnitude and duration of IOP reduction was evaluated in ocular normotensive monkeys. As shown in Table 4, a total of 900 μg of Compound II (hydrochloride) administered in three doses, ten minutes apart, resulted in significant IOP reduction.

TABLE 4

EFFECT OF REPEATED DOSES OF FASUDIL ON IOP IN THE
OCULAR NORMOTENSIVE CYNOMOLGUS MONKEY

| Compound | Baseline IOP (mmHg) | Percent Change from Baseline | | |
|---|---|---|---|---|
| | | 1 hr | 3 hr | 5 hr |
| Fasudil 900 μg OS | 20.6 ± 0.8 | 23.1 ± 2.8↓ | 23.1 ± 3.3↓ | 19.3 ± 3.2↓ |
| Vehicle 3 × 30 μl OS | 20.2 ± 0.8 | 4.1 ± 1.8↓ | 0.3 ± 4.4↑ | 1.1 ± 3.7↓ |

Fasudil was administered 3 × 30 μl topically (1 × 30 μl, 10 minutes apart). N = 10 for drug treated and N = 5 for vehicle. Fasudil was formulated in a phosphate buttered saline containing 0.01% benzalkonium chloride.

EXAMPLE 5

Topical Ophthalmic Formulation

| Ingredient | % (w/v) |
|---|---|
| Compound II (hydrochloride) | 1.5 |
| Benzalkonium chloride | 0.01 |
| Phosphate buffered saline | q.s. to 100 |

EXAMPLE 6

Topical Ophthalmic Formulation With Sustained Release

| Ingredient | % (w/v) |
|---|---|
| Compound II (hydrochloride) | 1.0 |
| Carbomer 934P or Carbomer 974P | 0.5 |
| NaCl | 0.4 |
| Mannitol | 2.4 |
| Disodium edetate | 0.01 |
| BAC | 0.01 |
| Water for Injection | q.s. to 100 |
| NaOH or HCl to adjust pH | q.s. |

EXAMPLE 7

Systemic Formulation (Oral)

| Ingredient | Weight Proportion |
|---|---|
| Compound II (hydrochloride) | 50 |
| Sodium Citrate | 20 |
| Alginic Acid | 5 |
| Polyvinylpyrrolidone | 15 |
| Magnesium Stearate | 5 |

Preparation: The dry composition is thoroughly blended, tablets are punched from the resulting mixture, each tablet being of such size that it contains 10 mg of Compound II (hydrochloride).

EXAMPLE 8

| Intraocular or Periocular Formulation (For Intravitreal for Periocular Injection) | |
|---|---|
| Ingredient | % (w/v) |
| Compound II (hydrochloride) | 0.002 |
| Sterile balanced salt solution | q.s. to 100 |

EXAMPLE 9

Method of Treatment (Topical)

A patient suffering from elevated IOP and/or visual field loss is treated by the topical administratration of the formulation of Example 5. One 30 μl drop of the formulation is administered one to four times per day to the affected eye(s) thereby reducing the IOP and/or the progression of visual field loss.

EXAMPLE 10

Method of Treatment (Systemic)

A patient suffering from elevated IOP and/or visual field loss is treated by the oral administration of the formulation of Example 7. One or more tablets of the formulation are administered orally 1 to 4 times per day thereby reducing the IOP and/or the progression of visual field loss.

EXAMPLE 11

Method of Treatment (Intraocular or Periocular)

A patient suffering from elevated IOP and/or visual field loss is treated by the intravitreal or periocular administration of the formulation of Example 8. Ten to twenty-five microliters of the formulation are administered 1 time per month to the affected eye(s) thereby reducing the IOP and/or the progression of visual field loss.

EXAMPLE 12

Other isoquinolinesulfonamides were topically administered to the eyes of New Zealand Albino (NZA) rabbits. The results are presented in Table 5 below.

TABLE 5

EFFECT OF OTHER ISOQUINOLINESULFONAMIDES ON IOP IN THE NZA RABBIT

| Compound | Baseline IOP (mmHg) | Percent Change from Baseline | | |
|---|---|---|---|---|
| | | 1 hr | 3 hr | 5 hr |
| 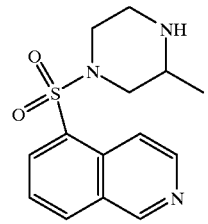 | 20.4 ± 0.8 | 14.6 ± 2.6 ↓ | 7.2 ± 4.1 ↓ | 0.9 ± 3.5 ↑ |
| 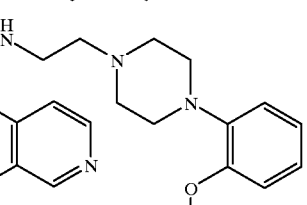 | 19.5 ± 0.5 | 7.7 ± 4.3 ↓ | 14.5 ± 0.5 ↓ | 0.8 ± 2.3 ↑ |
| 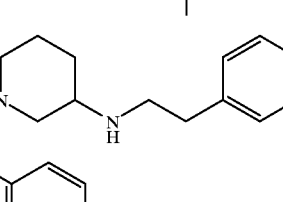 | 15.6 ± 0.5 | 16.8 ± 5.7 ↑ | 16.0 ± 5.7 ↑ | 37.0 ± 4.1 ↑ |
| 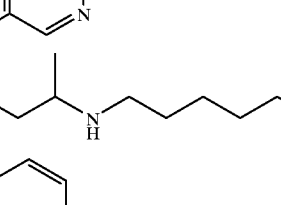 | 16.2 ± 0.3 | 9.9 ± 3.5 ↓ | 9.4 ± 1.9 ↓ | 3.3 ± 3.8 ↑ |

All drugs were administered to eyes in a topical manner at a dose=500 μg (2×25 μl). All compounds were formulated in phosphate buffered said containing 0.01% benzalkonium chloride, and in all instances N=7.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma, ocular hypertension, ocular ischemia and related disorders in a patient with one or more of such conditions, comprising administering to said patient a composition comprising an ophthalmically effective amount of a compound of formula:

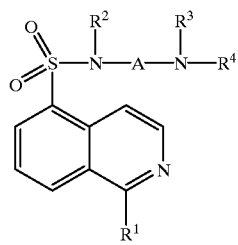

(I)

wherein $R^1$ represents a hydrogen atom, a chlorine atom or a hydroxyl group; and when $R^1$ represents a hydrogen atom, A represents an ethylene group unsubstituted or substituted with an alkyl group having 1 to 6 carbon atoms, a phenyl group or a benzyl group, $R^2$ and $R^3$ are directly bonded with each other, thereby forming a trimethylene group unsubstituted or substituted with an alkyl group having 1 to 6 carbon atoms, a phenyl group or a benzyl group, and $R^4$ represents a hydrogen atom or an alkyl group having 1 to 6 carbon atoms; with the proviso that the following compound be excluded:

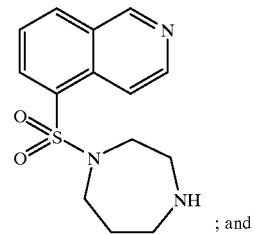

; and when $R^1$ represents a chlorine atom or a hydroxyl group,

A represents an alkylene group having 2 to 6 carbon atoms, said group being unsubstituted or substituted with an alkyl group having 1 to 6 carbon atoms, $R^2$ and $R^3$ are not bonded with each other and each independently represent a hydrogen atom or an alkyl group having 1 to 6 carbon atoms, or $R^2$ and $R^3$ are directly bonded with each other, thereby forming an ethylene group unsubstituted or substituted with an alkyl group having 1 to 6 carbon atoms or a trimethylene group unsubstituted or substituted with alkyl group having 1 to 6 carbon atoms, and $R^4$ represents a hydrogen atom, an alkyl group having 1 to 6 carbon atoms or an amidino group;

and pharmaceutically acceptable salts thereof; and an ophthalmically acceptable carrier therefore.

2. A method of treating glaucoma, ocular hypertension, ocular ischemia and related disorders in a patient with one or more of such conditions, comprising administering to said patient a composition consisting essentially of an ophthalmically acceptable carrier and an ophthalmically effective amount of a compound of formula:

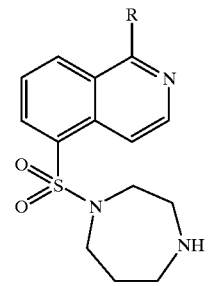

(III)

wherein R=H or OH;
and pharmaceutically acceptable salts thereof.

3. The method of claim 2, wherein the administration of the composition is effected topically.

4. The method of claim 2, wherein R=H.

5. The method of claim 4, wherein the final composition concentration of the compound is between about 0.001 and about 10.0 wt %.

6. The method of claim 5, wherein the final composition concentration of the compound is between about 0.01 and about 3.0 wt %.

7. The method of claim 6, wherein the final composition concentration of the compound is between about 0.1 and about 2.0 wt % and the pharmaceutically acceptable salt is hydrochloride.

8. The method of claim 2, wherein the composition further comprises a sustained release component.

9. The method of claim 8, wherein the sustained release component is selected from the group consisting of mucomimetic polymers, gelling polysaccharides, finely-divided drug carrier substrates, and combinations thereof.

* * * * *